United States Patent [19]

Haslam et al.

[11] Patent Number: 4,474,751
[45] Date of Patent: Oct. 2, 1984

[54] OPHTHALMIC DRUG DELIVERY SYSTEM UTILIZING THERMOSETTING GELS

[75] Inventors: John L. Haslam; Takeru Higuchi; Arthur R. Mlodozeniec, all of Lawrence, Kans.

[73] Assignee: Merck & Co., Inc., Rahway, N.J.

[21] Appl. No.: 495,238

[22] Filed: May 16, 1983

[51] Int. Cl.³ .................... A61K 31/74; A61K 31/70; A61K 31/135; A61K 31/54; A61K 31/415; A61K 31/435; A61K 31/19; A61K 31/66
[52] U.S. Cl. ........................................ 424/78; 424/85; 424/94; 424/114; 424/116; 424/177; 424/180; 424/181; 424/209; 424/211; 424/220; 424/221; 424/224; 424/230; 424/238; 424/243; 424/246; 424/248.51; 424/251; 424/253; 424/254; 424/256; 424/258; 424/263; 424/265; 424/267; 424/270; 424/271; 424/273 P; 424/273 R; 424/274; 424/275; 424/283
[58] Field of Search .................. 424/85, 94, 114, 116, 424/177, 180, 181, 209, 211, 220, 221, 224, 230, 238, 243, 246, 248.51, 251, 253, 254, 256, 258, 263, 265, 267, 270, 271, 273 P, 273 R, 313, 317, 321, 322, 324, 326, 330, 343, 274, 275, 283, 285, 300, 309, 311

[56] References Cited
U.S. PATENT DOCUMENTS

| 2,979,528 | 4/1961 | Lundsted | 260/584 |
| 3,711,604 | 1/1973 | Colodney et al. | 424/78 |
| 3,884,826 | 5/1975 | Phares et al. | 424/78 |
| 4,188,373 | 2/1980 | Kresanski | 424/177 |

FOREIGN PATENT DOCUMENTS 1072413 7/1976 Canada .

OTHER PUBLICATIONS

Journal of Pharm. & Pharmacology–"Novel Poloxamer & Poloxamine Hydrogels: Swelling & Drug Release" vol. 32, p. 5p, (1980), by A. Saden, A. J. Florence, T. L. Whateley.

Primary Examiner—Douglas W. Robinson
Attorney, Agent, or Firm—Manfred Polk; Michael C. Sudol, Jr.

[57] ABSTRACT

This invention describes the application of selected polymers as novel drug delivery systems which use the body temperature and pH to induce a liquid to gel transition of the polymer which contains a drug or therapeutic agent therein. The goal of such a delivery system is to achieve a greater degree of bioavailability or sustained concentration of a drug.

54 Claims, 2 Drawing Figures

OPHTHALMIC DRUG DELIVERY SYSTEM UTILIZING THERMOSETTING GELS

BACKGROUND OF THE INVENTION

A major loss of drugs administered to the eye is via the lacrimal drainage system so that only a small fraction of the dose remains in the eye for an extended period of time from a liquid drop formulation.

Different approaches have been taken to slow down this rapid loss of drug by using viscous solutions, gels, ointments and solid inserts.

Improvement in drug delivery has been achieved by these methods especially with the use of solid inserts where a large reduction in dose is possible while achieving the same therapeutic response as a liquid drop which must be administered more frequently and at higher drug concentration.

A principal advantage of the present invention is that it permits the accurate, reproducible unit dosing of a drug or active entity by using volumetric fluid delivery of the dosage prescribed while effecting the ultimate delivery of a semi-solid or rigid gel state. Conventionally, it is not possible to deliver preformed gels from multiple dose containers readily by volumetric means. Gravimetric dosing is thus required to achieve uniform content in delivering reproducible quantities. Conventionally, voids and packing or consolidation problems result when administering semi-solid preparations volumetrically. The present invention provides extremely accurate and uniform content of dose which is critical for many potent drugs.

A significant disadvantage to a solid insert however is that many patients have a difficult time inserting a solid object into the cul-de-sac of the eye and removing said solid object.

Another approach to these problems is to use a formulation which is a liquid at room temperature but which forms a semi-solid when warmed to body temperatures. Such a system has been described in U.S. Pat. No. 4,188,373 using "Pluronic ®) polyols" as the thermally gelling polymer. In this system the concentration of polymer is adjusted to give the desired sol-gel transition temperature, that is lower concentration of polymer gives a higher solution-gel (sol-gel) transition temperature. However, with the currently commercially available "Pluronic ®)" polymers the ability to obtain a gel of the desired rigidity is limited while maintaining the desired sol-gel transition temperature at physiologically useful temperature ranges near 26°–35° C.

Similarly Canadian patent 1072413 which relates to (poloxamer) gel systems with gelling temperatures higher than room temperature uses additives to bring about the gelling characteristics of the polymer which contains therapeutic or other type agents. Also in this Canadian patent "Tetronic ®)" polymers are used as additive agents rather than the primary polymeric agent as in the instant case.

SUMMARY OF THE INVENTION

The present invention provides a pharmaceutical vehicle which is useful in delivering pharmacologically active medicaments to the eye and in some cases as in dry eye using the vehicle alone. The drug delivery system consists of a clear physiologically-acceptable liquid which forms a semi-solid "gel" at human body temperatures. The sol-gel transition temperature and rigidity of the gel can be modified by changes in polymer concentration combined with the pH and ionic strength of the solution.

It has been discovered that certain polymers are useful vehicles having the properties set forth above. The polymers are tetra substituted derivatives of ethylene diamine (poloxamine, w=2 in Formula I), propylene diamine (w=3), butylene diamine (w=4), pentylene diamine (w=5) or hexylene diamine (w=6). The substituents are block copolymers of poly(oxypropylene) and poly(oxyethylene) of various chain lengths and ratios x to y in the general formula of the polymer shown below.

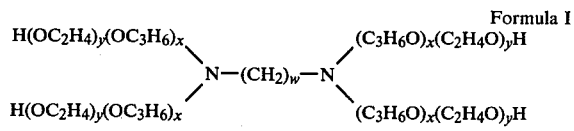

Formula I wherein w is an integer from 2 through 6.

A typical polymer system of our invention would contain a polymer containing approximately 40 to 80% poly(oxyetnylene) and approximately 20 to 60% poly(oxypropylene). The total molecular weight of the polymer used in our invention is at a minimum about 7,000 and can go as high as 50,000 but preferably is in the range of 7,000 to 30,000; and x and y are any integers within the above constraints. Preferred polymers are those of the formula above where w=2, namely the poloxamine polymer.

The aqueous drug delivery vehicle would contain from 10% to 50% by weight of the entire vehicle as polymer described above. The aqueous drug delivery vehicle would also contain the drug or therapeutic agent in addition to various additives such as acids or bases to adjust the pH of the composition, buffers to maintain the pH, preservatives to control bacterial contamination, other additives to provide for drug solubility and stability and formulation performance with purified water making up the remainder of the drug delivery vehicle.

DETAILED DESCRIPTION OF THE INVENTION

The invention consists of a pharmaceutical composition or drug delivery system which is a clear physiological acceptable solution at room temperature or lower but which forms a semi-solid or gel when placed in the eye. The unique feature of this system is that both the gel transition temperature and/or the rigidity of the gel can be modified by adjustment of the pH and or ionic strength and polymer concentration.

The ability to change the sol-gel transition temperature by pH adjustment is a critical feature of the invention which overcomes many of the disadvantages of previous approaches. Also the sol-gel transition temperature can be modified somewhat by ionic strength adjustment.

An example of a drug delivery vehicle in accordance with this invention consists of an aqueous solution of, for example, a tetra substituted ethylene diamine block copolymer of poly(oxyethylene)-poly(oxypropylene) (where w=2 in Formula I) in which the substitution at the nitrogen is to the poly(oxypropylene) block and the polymer consists of about 40–80% as the poly(oxyethylene) unit and about 20–60% as the polypropylene unit and which has a total average molecular weight of 7,000 to 50,000 with a preferred range of 7,000–30,000. Such polymers are included in the polymers sold under the trademark "Tetronic ®" polyols by BASF Wyandotte Corporation.

Other polymers where w=3 to 6 (of Formula I) can be made according to methods known in the art (Block and Graft Copolymerization, Vol. 2 edited by R. J. Ceresa published by John Wiley and Sons, 1976) by using the appropriate initiators such as for example propylenediamine, butylenediamine, pentylenediamine and hexylenediamine.

The preferred polymers are those which form gels at a concentration range of 10 to 50% of the polymer to water.

A good example of a typical polymer used in the drug delivery system of our invention is Tetronic ® 1307 which thermally gels over a concentration range of about 15% to 35% in water with gelling temperatures of about 30° C. to 10° C. at neutral pH. The gel strength at 35% concentration is much more rigid than at the 15% gel concentration. However, with a solution-gel transition temperature of about 10° C. for the 35% solution any useful liquid product would have to be refrigerated below this temperature. A useful vehicle can be prepared however by modification of both concentration and pH. For example a 27% Tetronic ® 1307 solution at neutral pH has a gel-sol transition temperature of about 16° C. but at pH 4 (adjusted to such with HCl at 10° C.) the transition temperature is about 25° C. The gel formed under these conditions meets the requirements of a fairly rigid gel which is a liquid at room temperature.

Figure 1:
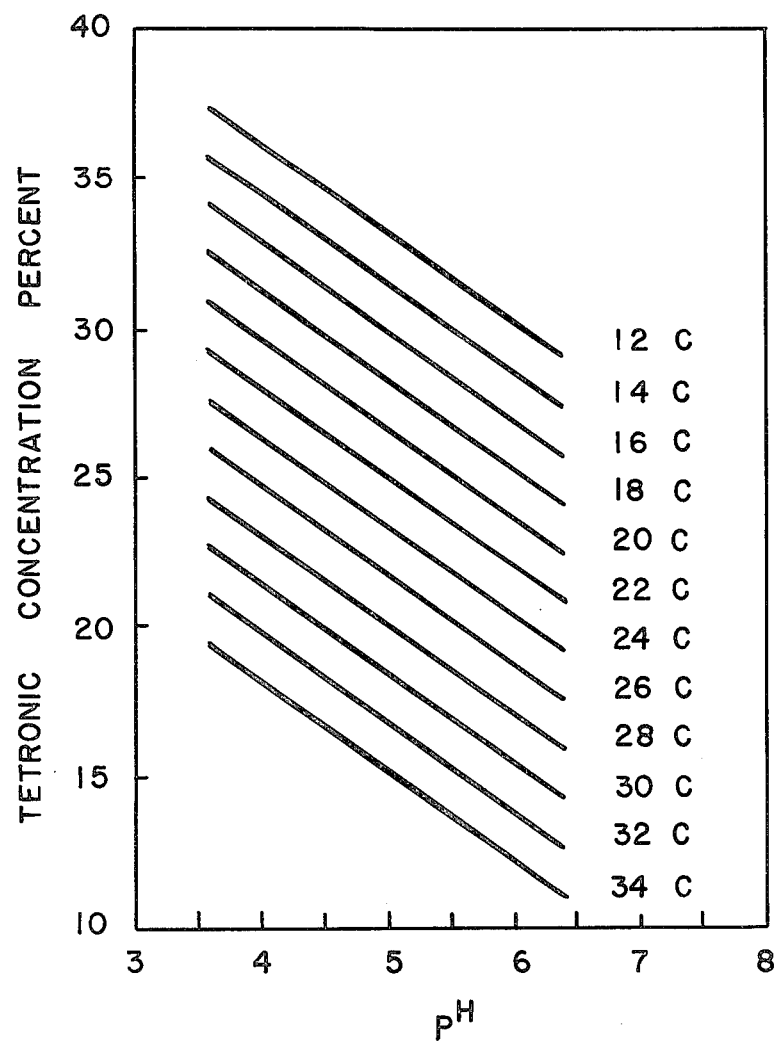

The effect of pH and polymer concentration on gelling temperature for Tetronic ® 1307 is shown in FIG. 1. Thus, for example, at a concentration of polymer to water of 25% the gelling temperature is 19° C. at pH 6 and increases to 26° C. at pH 4.

For administration of the drug delivery system of our invention to the eye as drops, the pH of the system can range from 2 to 9 with the preferred pH range being 4 to 8. The pH, concentration and gelling temperatures will vary for any individual polymer falling within the class covered in this invention and these factors can be determined by those skilled in the art in possession of this concept.

The pH of the drug delivery system is adjusted by adding the appropriate amount of a pharmaceutically acceptable acid or base to obtain the required pH. The acid or base can be any that are known to persons skilled in the art but are preferably hydrochloric acid or sodium hydroxide.

In general the ophthalmic drug delivery vehicle of the present invention will contain from about 0.01 to about 5% of the medicament or pharmaceutical, from about 10% to about 50% of the polymer and from 90% to about 45% water. In special situations, however, the amounts may be varied to increase or decrease the dosage schedule.

If desired, the drug delivery vehicle may also contain, in addition to the medicament, buffering agents and preservatives. Suitable water soluble preservatives which may be employed in the drug delivery vehicle are sodium bisulfite, sodium thiosulfate, ascorbate, benzalkonium chloride, chlorobutanol, thimerosal, phenylmercuric borate, parabens, benzyl alcohol and phenylethanol. These agents may be present in amounts of from 0.001 to 5% by weight and preferably 0.01 to 2%. Suitable water soluble buffering agents are alkali or alkali earth carbonates, phosphates, bicarbonates, citrates, borates, acetates, succinates and the like, such as sodium phosphate, citrate, borate, acetate, bicarbonate and carbonate. These agents may be present in amounts sufficient to maintain a pH of the system of between 2 to 9 and preferably 4 to 8. As such the buffering agent can be as much as 5% on a weight to weight basis of the total composition.

Another factor which can affect the gelling temperature of the drug delivery vehicle or pharmaceutical composition is its ionic strength and this can be varied by adding to the drug delivery vehicle a pharmaceutically acceptable salt, such as sodium chloride, potassium chloride or mixtures thereof or even suitable alkali metal salts such as sodium sulfate and the like. The effect of adding sodium chloride is to decrease the gelling temperature by about 3° C. for a change of 0.2 molar in ionic strength. Fortunately for a typical ophthalmic dosage the pH and ionic strength effects will help maintain the drug delivery system as a gel in the eye. For example, a 27% thermally gelling solution (thermogel) at pH 4 and low ionic strength (about 0) when in the eye will be bathed with pH 7.4 and isotonic lacrimal fluid which at the surface of the gel will act to lower the gel-sol transition temperature thus helping to maintain and insure a gelled formulation in the eye rather than having the drug delivery system liquefy and perhaps be eliminated rapidly from the eye through the lacrimal drainage system.

Figure 2:
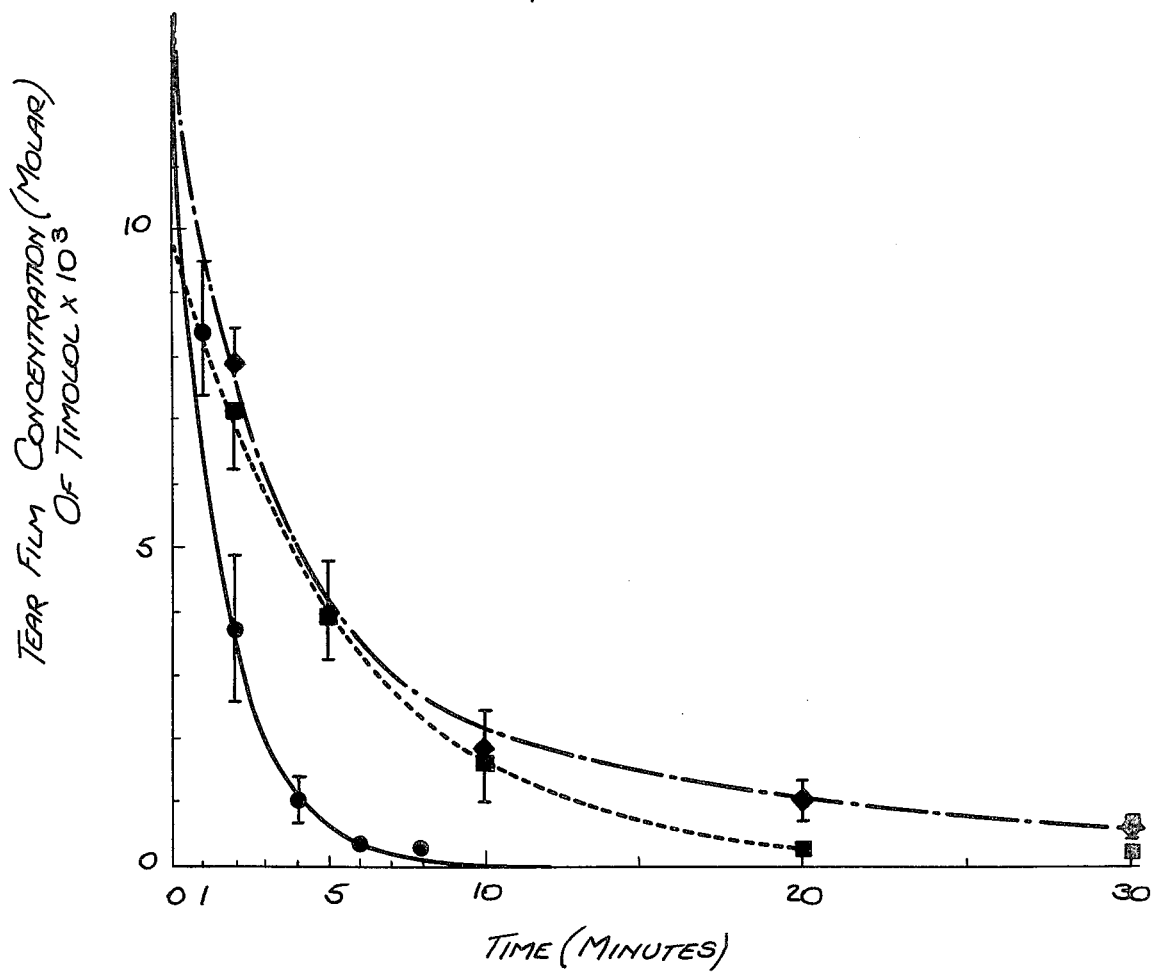

A unique aspect of the gel which is formed in situ in the eye or preferably in the inferior cul-de-sac of the eye is its prolonged residence time compared to conventional ophthalmic solutions. The tear turnover usually dilutes and depletes the drug reservoir very rapidly in conventional solutions. The thermogel formulation dissolves more slowly and promotes an enhanced delivery of the dissolved or dispersed agent within it. This prolonged residence time leads to more effective levels of concentration of agent in the tear film. An example of this longer residence time of the drug in the tear film is shown in FIG. 2. The two thermogel formulations show a higher concentration of timolol for an extended period of time than the conventional marketed product. A dose sparing effect on the total amount of drug or agent applied and greater therapeutic effectiveness can be achieved with the thermogel formulations due to higher concentration of agent in the tear film when the agent penetrates the eye if this is desired or within the tear film if penetration is not desired.

Any pharmaceutically active material or diagnostic agent may be delivered in the drug delivery system of this invention. Preferably the drug or pharmaceutical is water soluble although some drugs will show greater solubility in the polymer system than others. Also the drugs or diagnostic agents can be suspended in the polymer vehicle.

Suitable drugs or diagnostic agents which can be administered by the drug polymer delivery system of the present invention that might be mentioned are:

(1) antibacterial substances such as beta-lactam antibiotics, such as cefoxitin, n-formamidoyl-thienamycin and other thienamycin derivatives, tetracyclines, chloramphenicol, neomycin, carbenicillin, colistin, penicillin G, polymyxin B, vancomycin, cefazolin, cephaloridine, chibrorifamycin, gramicidin, bacitracin, sulfonamides; aminoglycoside antibiotics such as gentamycin, kanamycin, amikacin, sisomicin and tobramycin; naladixic acid and analogs such as norfloxacin and the antimicrobial combination of fluealanine/pentizidone; nitrofurazones, and the like;

(2) antihistaminics and decongestants such as pyrilamine, chlorpheniramine, tetrahydrazoline, antazoline, and the like;

(3) anti-inflammatories such as cortisone, hydrocortisone, hydrocortisone acetate, betamethasone, dexamethasone, dexamethasone sodium phosphate, prednisone, methylprednisolone, medrysone, fluorometholone, fluocortolone, prednisolone, prednisolone sodium phosphate, triamcinolone, indomethacin, sulindac, its salts and its corresponding sulfide, and the like;

(4) miotics and anticholinergics such as echothiophate, pilocarpine, physostigmine salicylate, diisopropylfluorophosphate, epinephrine, dipivolyl epinephrine, neostigmine, echothiopate iodide, demecarium bromide, carbachol, methacholine, bethanechol, and the like;

(5) mydriatics such as atropine, homatropine, scopolamine, hydroxyamphetamine, ephedrine, cocaine, tropicamide, phenylephrine, cyclopentolate, oxyphenonium, eucatropine, and the like; and other medicaments used in the treatment of eye conditions or diseases such as (6) antiglaucoma drugs for example, timolol, especially as the maleate salt and R-timolol and a combination of timolol or R-timolol with pilocarpine. Also included are: epinephrine and epinephrine complex or prodrugs such as the bitartrate, borate, hydrochloride and dipivefrin derivatives and hyperosmotic agents such as glycerol, mannitol and urea;

(7) antiparasitic compounds and/or anti-protozoal compounds such as ivermectin; pyrimethamine, trisulfapyrimidine, clindamycin and corticosteroid preparations;

(8) antiviral effective compounds such as acyclovir, 5-iodo-2'-deoxyuridine (IDU), adenosine arabinoside (Ara-A), trifluorothymidine, and interferon and interferon inducing agents such as Poly I:C;

(9) carbonic anhydrase inhibitors such as acetazolamide, dichlorphenamide, 2-(p-hydroxyphenyl)thio-5-thiophenesulfonamide, 6-hydroxy-2-benzothiazolesulfonamide and 6-pivaloyloxy-2-benzothiazolesulfonamide;

(10) anti-fungal agents such as amphotericin B, nystatin, flucytosine, natamycin, and miconazole;

(11) anesthetic agents such as etidocaine cocaine, benoxinate, dibucaine hydrochloride, dyclonine hydrochloride, naepaine, phenacaine hydrochloride, piperocaine, proparacaine hydrochloride, tetracaine hydrochloride, hexylcaine, bupivacaine, lidocaine, mepivacaine and prilocaine;

(12) ophthalmic diagnostic agents such as
  (a) those used to examine the retina and choride-sodium fluorescein;
  (b) those used to examine the conjunctiva, cornea and lacrimal apparatus such as fluorescein and rose bengal; and
  (c) those used to examine abnormal pupillary responses such as methacholine, cocaine, adrenaline, atropine, hydroxyamphetamine and pilocarpine;

(13) ophthalmic agents used as adjuncts in surgery such as alpha-chymotrypsin, and hyaluronidase;

(14) chelating agents such as ethylenediamine tetraacetate (EDTA) and deferoxamine;

(15) immunosuppressive agents and anti-metabolites such as methotrexate, cyclophosphamide, 6-mercaptopurine, and azathioprine; and

(16) combinations of the above such as antibiotic/anti-inflammatory as in neomycin sulfate-dexamethasone sodium phosphate, concomitant anti-glaucoma therapy such as timolol maleate-aceclidine.

Typically as stated previously, the present liquid drug delivery device would contain from about 0.001 to about 5% of the medicament or pharmaceutical on a weight to weight basis. Thus, from one drop of the liquid composition which contains about 25 mg of solution, one would obtain about 0.0025 mg to about 1.25 mg of drug.

The particular drug or medicament used in the pharmaceutical composition of this invention is the type which a patent would require for pharmacological treatment of the condition from which said patient is suffering. For example, if the patient is suffering from glaucoma, the drug of choice would probably be timolol.

Also included in this invention is the use of the drug delivery device or pharmaceutical composition minus the active drug or medicament for the treatment of dry eye. All the ratios of components as described above would be satisfactory for the composition used for dry eye. For this use, one would administer drops as needed.

The preparation of the drug delivery systems are described below and the appropriate examples which follow were all carried out according to this procedure. Since the polymer systems of this invention dissolve better at reduced temperatures, the preferred methods of solubilization are to add the required amount of polymer to the amount of water to be used. Generally, after wetting the polymer by shaking, the mixture is capped and placed in a cold chamber or in a thermostated container at about 0° C. to 10° C. to dissolve the polymer. The mixture can be stirred or shaken to bring about a more rapid solution of the polymer.

The drug substance or medicaments and various additives such as buffers, salts and preservatives are then added and dissolved. The final desired pH adjustment can be made by adding the appropriate acids or bases such as hydrochloric acid or sodium hydroxide to the drug delivery system.

When used in the eye the pharmaceutical composition will be administered as a fluid by any conventional means of delivering drop formulations to the eye such as by means of an eye-dropper or by using an Ocumeter ®. Typically these formulations are intended to be administered into the inferior cul-de-sac of the eye. This can easily be accomplished by distending the lower lid from the eye and applying the drop within the sac and then releasing the lid.

EXAMPLES

The following examples are illustrations and are not intended to be restrictive of the scope of the invention.

All percentages are given in (w/w) % and all pH measurements are for 10° C. In the animal experiments, 25 mg of each solution was administered to tne inferior cul-de-sac of the eye.

EXAMPLE 1

The use of the polymer vehicle to deliver pilocarpine.

|  | Solution 1 | Solution 2 | Solution 3 |
|---|---|---|---|
| Pilocarpine | 0.5% | 0.1% | 0.5% |
| Tetronic 1307 | 27.0% | 27.0% | — |
| pH adjusted with HCl to | 4.0 | 4.0 | 4.0 |
| sufficient purified water to make | 100% | 100% | 100% |
| gel-sol transition temp. | 26° C. | 26° C. | — |

Pilocarpine is known to produce a miotic effect (constriction of the iris). In an experiment in rabbits the miotic effect of pilocarpine in the thermally gelling solutions 1 and 2 was compared with solution 3, a conventional liquid drop. The pupillary diameter change was measured over 3 hours. The results showed solution 1 had a larger area under the curve than 2 or 3 and that solutions 2 and 3 had about the same AUC. The relative area under the curve measurements:

| Solution | Relative AUC |
|---|---|
| 1 | 1.3 |
| 2 | 0.9 |
| 3 | 1.0 |

These results indicate about a 5-fold reduction in pilocarpine concentration in the thermally gelling solution (solution 2) can produce a similar pharmacological response as a conventional drop (solution 3).

EXAMPLE 2

The use of the polymer vehicle to deliver timolol.

|  | Solution 1 | Solution 2 |
|---|---|---|
| Timolol maleate | 0.68% | 0.68% |
| Tetronic 1307 | 22.0% | 27.0% |
| pH adjusted with HCl to | 4 | 4 |
| sufficient water to make | 100% | 100% |
| gel-sol transition temperature | 30° | 26° |

The thermally gelling solutions 1 and 2 were compared to the commercially available Timoptic ® solution (Timolol maleate 0.68%). The experiment involved measurement of the lacrimal fluid concentration of the drug with time. Even though a biological response is not measured, the effect of the thermally gelling solutions in maintaining higher drug concentrations for extended periods of time provides an indication of the response the drug should have. The solutions can be compared from the first-order decay rates and AUC.

| Solution | Half-life | Relative AUC |
|---|---|---|
| Solution 1 | 3.8 min. | 2.7 |
| Solution 2 | 13 min. | 3.3 |
| Timoptic[R] | 1.1 min. | 1 |

The thermally gelling solutions provide much slower elimination rates of the drug from eye.

EXAMPLE 3

The use of the polymer vehicle to deliver Norfloxacin.

|  | Solution 1 | Solution 2 | Solution 3 | Solution 4 |
|---|---|---|---|---|
| Norfloxacin | 0.1% | 0.1% | 0.1% | 0.1% |
| Tetronic 1307 | 22.0% | 27.0% | 32.0% | — |
| pH adjusted with HCl to | 4 | 4 | 4 | 4 |
| sufficient purified water to make | 100% | 100% | 100% | 100% |
| gel-sol transition temp. | 30° C. | 26° C. | 21° C. | — |

The concentration of norfloxacin was measured in the lacrimal fluid with time. The elimination rates of norfloxacin were slower for the thermally gelling solutions 1, 2 and 3 and produced larger AUC.

| Solution | Relative AUC |
|---|---|
| 1 | 2.2 |
| 2 | 1.7 |
| 3 | 1.9 |
| 4 | 1 |

EXAMPLE 4

|  | Solution 1 | Solution 2 |
|---|---|---|
| Norfloxacin | 0.4% | 0.2% |
| Tetronic 1307 | 27.0% | 0.0% |
| pH adjusted with HCl to | 4 | 4 |
| sufficient purified water to make | 100% | 100% |

The solutions in Example 4 can be used to demonstrate that a larger dose of drug can be administered in the thermally gelling solution without exceeding the saturation level of the drug. Solutions 1 and 2 in the rabbit eye both give initial concentrations of about 2 mg/ml even though solution 1 has twice the concentration. The slower release from such a thermally gelling solutions would be of value under such conditions.

EXAMPLE 5

| Dexamethasone | 0.05% |
|---|---|
| Tetronic 1307 | 30.0% |
| Benzalkonium chloride | 0.02% |
| pH adjusted with HCl to | 4 |
| sufficient purified water to make | 100% |
| gel-sol transition temperature | 21° |

EXAMPLE 6

| Gentamycin Sulfate | 0.1% |
|---|---|
| Tetronic 1307 | 25.0% |
| Benzalkonium chloride | 0.01% |
| Sodium chloride | 0.05% |
| pH adjusted with HCl to | 4 |
| sufficient purified water to make | 100% |
| gel-sol transition temperature | 26° |

EXAMPLE 7

| | |
|---|---|
| Chloramphenicol | 0.5% |
| Tetronic 1508 | 20.0% |
| Sodium acetate | 0.3% |
| Benzalkonium chloride | 0.01% |
| pH adjusted with HCl to | 5 |
| sufficient purified water to make | 100% |
| gel-sol transition temperature | 27° |

If the pharmaceutical compositions of Examples 5-7 were compared with similar compositions but without the polymer, it would be expected that the compositions of Examples 5-7 would result in greater bioavailability and/or sustained concentrations of the drug in the eye.

Following the procedure of Examples 1-6 one can use an appropriate amount of the polymers listed below in place of the Tetronic 1307 or Tetronic 1508 polymer used in Examples 1-6 and 7.

Tetronic 1107
Tetronic 908
Tetronic 707

Following the procedure of Examples 1-7 one can use an appropriate amount of the drugs or medicaments previously enumerated in this application in place of the drug or medicament used in Examples 1-7.

What is claimed is:

1. An aqueous pharmaceutical composition for treating an eye condition requiring pharmacological treatment comprising
   a. 10% to 50% by weight of a polymer of the formula

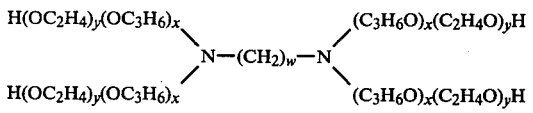

wherein w is an integer from 2 to 6 containing approximately 40% to 80% poly(oxyethylene) and approximately 20 to 60% poly(oxypropylene) and having a molecular weight of 7,000 to 50,000; and x and y are any integers within the above constraints,
   b. a pharmacologically effective amount of a pharmaceutical or diagnostic agent; and,
   c. a pharmaceutically acceptable acid or base being in sufficient quantity to adjust the pH of the composition to range from 2 to 9 and wherein the composition is liquid at about room temperature or below.

2. An aqueous pharmaceutical composition for treating an eye condition requiring pharmacological treatment comprising
   a. 10% to 50% by weight of a polymer of the formula

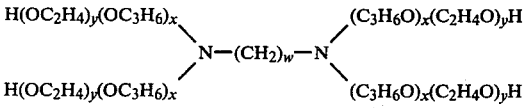

wherein w is an integer of from 2 to 6 containing approximately 40% to 80% poly(oxyethylene) and approximately 20 to 60% poly(oxypropylene) and having a molecular weight of 7,000 to 50,000; and x and y are any integers within the above constraints,
   b. a pharmacologically effective amount of a drug selected from the group consisting of antibacterial substances, antihistamines and decongestants, antiinflammatories, miotics and anticholinergics, mydriatics, antiglaucoma drugs, antiparasitics, antiviral effective compounds, carbonic anhydrase inhibitors, anesthetic agents, ophthalmic diagnostic agents, ophthalmic agents used as adjuvants in surgery, chelating agents, immunosuppressive agents and anti-metabolites or combinations of any of the above; and,
   c. a pharmaceutically acceptable acid or base being in sufficient quantity to adjust the pH of the composition to range from 2 to 9 and wherein the composition is liquid at about room temperature or below.

3. The composition of claim 2 wherein the polymer is one where w is 2.

4. The composition of claim 2 wherein the polymer is Tetronic 1307 ®.

5. The composition of claim 2 wherein the gel-sol transition temperature of the composition is room temperature or below and said composition is liquid at this temperature.

6. The composition of claim 2 wherein the antibacterial substances are selected from the group consisting of beta lactam antibiotics, tetracyclines, carbenicillin, colistin, penicillin G, polymyxin B, vancomycin, chloramphenicol, neomycin, gramicidin, bacitracin, cefazolin, cephaloridine, chibrorifamycin, sulfonamides, aminoglycoside antibiotics, tobramycin, nitrofurazone, nalidixic acid and norfloxacin and the antimicrobial combination of fludalanine/pentizidone.

7. The composition of claim 2 wherein the antihistaminics and decongestants are selected from the group consisting of perilamine, chlorpheniramine, tetrahydrazoline and antizoline.

8. The composition of claim 2 wherein the antiinflammatory drugs are selected from the group consisting of hydrocortisone acetate, cortisone, hydrocortisone, betamethasone, dexamethasone, fluocortolone, prednisolone, methyl prednisolone, medrysone, fluorometholone, prednisolone sodium phosphate, triamcinolone, indomethacin, sulindac and its salts and corresponding sulfide.

9. A composition of claim 2 wherein the miotics and anticholinergics are selected from the group consisting of echothiophate, pilocarpine, physostigmine salicylate, diisopropylfluorophosphate, carbachol, methacholine, bethanechol, epinephrine, dipivefrin, neostigmine, echothiopateiodide and demecium bromide.

10. The composition of claim 2 wherein the mydriatics are selected from the group consisting of atropine, homatropine, scopolamine, hydroxyamphetamine, ephedrine, cocaine, tropicamide, phenylephrine, cyclopentolate, oxyphenonium and eucatropine.

11. The composition of claim 2 wherein the antiglaucoma drugs are selected from the group consisting of timolol, R-timolol, the hydrogen maleate salt of timolol, the combination of timolol and R-timolol with pilocarpine, epinephrine and epinephrine complex or prodrugs and hyperosmotic agents.

12. A composition of claim 2 wherein the antiparasitic or antiprotozoal compound is ivermectin, pyrimethamine, trisulfapyrimidone, clindamycin and corticosteroid preparations.

13. The composition of claim 2 wherein the antiviral effective compounds are selected from the group consisting of acyclovir, interferon, 5-iodo-2'-deoxyuridine, adenosine, arabinoside and trifluorothymidine.

14. The composition of claim 2 wherein the carbonic anhydrase inhibitors are selected from the group consisting of 2-(p-hydroxyphenyl)thio-5-thiophenesulfonimide, 6-hydroxy-2-benzothiazolsulfonamide, 6-pivaloyloxy-2-benzothiazolesulfonamide, acetazolamide, and dichlorphenamide.

15. The composition of claim 2 wherein the antifungal agents are selected from the group consisting of amphoterium B, nystatin, flucytosine, natamycin and miconazole.

16. The composition of claim 2 wherein the anesthetic agent is selected from the group consisting of etidocaine, cocaine, benoxinate, dibucaine hydrochloride, dyclonine hydrochloride, naepaine, phenacaine hydrochloride, piperocaine, proparacaine hydrochloride, tetracaine hydrochloride, hexylcaine, bupivacaine, lidocaine, mepivacaine and prilocaine.

17. The composition of claim 2 wherein the chelating agent is selected from the group consisting of ethylenediamine tetra-acetate and deferoxamine.

18. The composition of claim 2 wherein the immunosuppressive agent and anti-metabolite is selected from the group consisting of methotrexate, cyclophosphamide, 6-mercaptopurine and azathioprine.

19. The composition of claim 2 which includes a buffering agent or salt of from 0 to 5% by weight of the composition.

20. The composition of claim 19 wherein the buffering agent or salt is selected from the group consisting of alkali or alkali earth carbonates, chlorides, sulfates, phosphates, bicarbonates, citrates, borates, acetates and succinates.

21. The composition of claim 2 which includes from 0.001% to 5% by weight of the composition of a preservative.

22. The composition of claim 21 wherein the preservatives are selected from the group consisting of sodium bisulfite, sodium thiosulfate, ascorbate, benzalkonium chloride, chlorobutanol, thimerosal, phenylmercuric borate, parabens, benzylalcohol and phenylethanol.

23. The composition of claim 2 wherein the acid or base is selected from the group consisting of hydrochloric acid or sodium hydroxide.

24. An aqueous pharmaceutical composition for treating an eye condition requiring pharmacological treatment comprising
a. 10% to 50% by weight of a polymer of the formula

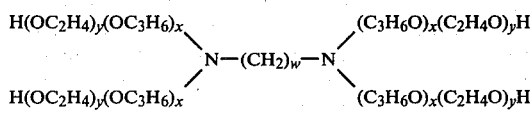

wherein w is an integer of from 2 to 6 containing approximately 40% to 80% poly(oxyethylene) and approximately 20-60% poly(oxypropylene) and having a molecular weight of 7,000 to 50,000; and x and y are any integers within the above constraints; and,
b. a pharmaceutically acceptable acid or base being in sufficient quantity to adjust the pH of the composition to range from 2 to 9.

25. A composition of claim 24 which includes a buffering agent or salt of from 0 to 5% by weight of the composition.

26. A composition of claim 24 which includes a preservative of from 0.001% to 5% by weight of the composition.

27. A method of treating an eye condition requiring pharmacological treatment or administration of a diagnostic agent which comprises administering to the eye a liquid drug delivery vehicle comprising:
a. 10% to 50% by weight of a polymer of the formula

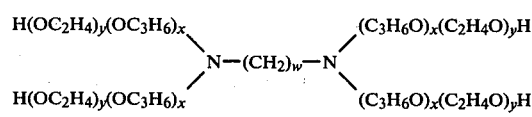

wherein w is an integer of from 2 to 6 containing approximately 40% to 80% poly(oxyethylene) and approximately 20-60% poly(oxypropylene) and having a molecular weight of 7,000 to 50,000; and x and y are any integers within the above constraints,
b. a pharmacologically effective amount of a pharmaceutical or diagnostic agent; and,
c. a pharmaceutically acceptable acid or base being in sufficient quantity to adjust the pH of the composition to range from 2 to 9.

28. A method of treating an eye condition requiring pharmacological treatment or administration of a diagnostic agent which comprises administering to the eye a liquid drug delivery vehicle comprising:
a. 10% to 50% by weight of a polymer of the formula

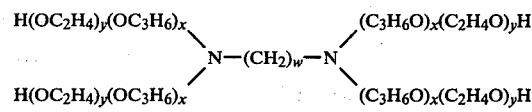

wherein w is an integer of from 2 to 6 containing approximately 40% to 80% poly(oxyethylene) and approximately 20-60% poly(oxypropylene) and having a molecular weight of 7,000 to 50,000; and x and y are any integers within the above constraints,
b. a pharmacologically effective amount of a drug selected from the group consisting of antibacterial substances, antihistamines and decongestants, anti-inflammatories, miotics and anticholinergics, mydriatics, antiglaucoma drugs, antiparasitics, antiviral effective compounds, carbonic anhydrase inhibitors, anesthetic agents, opthalmic diagnostic agents, opthalmic agents used as adjuvants in surgery, chelating agents, immunosuppressive agents and antimetabolites or combinations of the above; and
c. a pharmaceutically acceptable acid or base being in sufficient quantity to adjust the pH of the composition to range from 2 to 9.

29. A method of treatment according to claim 28 wherein the polymer is one wherein w=2.

30. A method of treatment according to claim 28 wherein the polymer is Tetronic 1307 ®.

31. A method of treatment according to claim 28 wherein the gel-sol transistion temperature of the composition is room temperature or below and said composition is liquid at this temperature.

32. A method of treatment according to claim 28 wherein the antibacterial substances are selected from the group consisting of beta-lactam antibiotics, tetracyclines, carbenicillin, colistin, penicillin G, polymyxin B, vancomycin, chloramphenicol, neomycin, gramicidin, bacitracin, cefazolin, cephaloridine, chibro-rifamycin, sulfonamides, aminoglycoside antibiotics, tobramycin, nitrofurazone, nalidixic acid and analogs and the antimicrobial combination of fludalanine/pentizidone.

33. A method of treatment according to claim 28 wherein the antihistaminics and decongestants are selected from the group consisting of perilamine, chlorpheneramine, tetrahydrazoline and antizoline.

34. A method of treatment according to claim 28 wherein the antiinflammatory drugs are selected from the group consisting of hydrocortisone acetate, cortisone, hydrocortisone, betamethasone, dexamethasone, fluocortolone, prednisolone, methyl prednisolone, medrysone, fluorometholone, prednisolone sodium phosphate, triamcinolone, indomethacin, sulindac and its salts and corresponding sulfide.

35. A method of treatment of claim 28 wherein the miotics and anticholinergics are selected from the group consisting of echothiophate, pilocarpine, physostigmine salicylate, diisopropylfluorophosphate, carbachol, methacholine, bethanechol, epinephrine, dipivalylepinephrine, neostigmine, echothiopateiodide and demecium bromide.

36. A method of treatment according to claim 28 wherein the mydriatics are selected from the group consisting of atropine, homatropine, scopolamine, hydroxyamphetamine, ephedrine, cocaine, tropicamide, phenylephrine, cyclopentolate, oxyphenonium and eucatropine.

37. A method of treatment according to claim 28 wherein the antiglaucoma drugs are selected from the group consisting of timolol, R-timolol, the hydrogen maleate salt of timolol, the combination of timolol and R-timolol with pilocarpine, epinephrine, dipivefrin and epinephrine complex or prodrugs and hyperosmotic agents.

38. A composition of claim 28 wherein the antiparasitic or anti-protozoal compound is ivermectin, pyrimethaxine, trisulfapyrimidon, clindamycin and corticosteroid preparations.

39. A method of treatment according to claim 28 wherein the antiviral effective compounds are selected from the group consisting of acyclovir, interferon, 5-iodo-2'-deoxy uridine, adenosine, arabinoside and trifluorothymidine.

40. A method of treatment according to claim 28 wherein the carbonic anhydrase inhibitors are selected from the group consisting of 2-(p-hydroxyphenyl)thio-5-thiophenesulfonimide, 6-hydroxy-2-benzothiazolesulfonamide, 6-pivaloyloxy-2-benzothiazolesulfonamide, acetazolamide and dichlorphenamide.

41. The method of treatment according to claim 28 wherein the antifungal agents are selected from the group consisting of amphoterium B, nystatin, flucytosine, natamycin and miconazole.

42. The method of treatment according to claim 28 wherein the anesthetic agent is selected from the group consisting of etidocaine, cocaine, benoxinate, dibucaine hydrochloride, dyclonine hydrochloride, naepaine, phenacaine hydrochloride, piperocaine, proparacaine hydrochloride, tetracaine hydrochloride, hexylcaine, bupivacaine, lidocaine, mepivacaine and prilocaine.

43. The method of treatment according to claim 28 wherein the chelating agent is selected from the group consisting of ethylenediamine tetra-acetate and deferoxamine.

44. The method of treatment according to claim 28 wherein the immunosuppressive agent and anti-metabolite is selected from the group consisting of methotrexate, cyclophosphamide, 6-mercaptopurine and azathioprine.

45. A method of treatment according to claim 28 wherein the composition includes a buffering agent or salt of from 0% to 5% by weight of the composition.

46. A method of treatment according to claim 45 wherein the buffering agent or salt is selected from the group consisting of alkali or alkali earth carbonates, chlorides, sulfates, phosphates, bicarbonates, citrates, borates, acetates and succinates.

47. A method of treatment according to claim 28 wherein the composition includes from 0.001% to 5% by weight of the composition of a preservative.

48. A method of treatment according to claim 47 wherein the preservatives are selected from the group consisting of sodium bisulfite, sodium thiosulfate, ascorbate, benzalkonium chloride, chlorobutanol, thimerosal, phenylmercuric borate, parabens, benzylalcohol and phenylethanol.

49. A method of treatment according to claim 28 wherein the acid or base is selected from the group consisting of hydrochloric acid or sodium hydroxide.

50. A methou of treating a dry eye which comprises administering to the eye a liquid drug delivery device comprising
  a. 10% to 50% by weight of a polymer of the formula

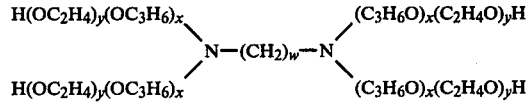

wherein w is an integer of from 2 to 6 containing approximately 40% to 80% poly(oxyethylene) and approximately 20–60% poly(oxypropylene) and having a molecular weight of 7,000 to 50,000; and x and y are any integers within the above constraints; and,
  b. a pharmaceutically acceptable acid or base being in sufficient quantity to adjust the pH of the composition to range from 2 to 9.

51. A method of treatment of claim 50 wherein the composition includes a buffering agent or salt of from 0% to 5% by weight of the composition.

52. A method of treatment of claim 50 wherein the composition includes a preservative of from 0.001% to 5% by weight of the composition.

53. The composition of claim 6 wherein the β-lactam antibiotics are selected from the group consisting of cefoxitin, n-formamidoyl thienamycin and other thienamycin derivatives.

54. A method of treatment of claim 32 wherein the β-lactam antibiotics are selected from the group consisting of cefoxitin, n-formamidoyl thienamycin and other thienamycin derivatives.

* * * * *